United States Patent [19]

Stütz

[11] Patent Number: 4,742,077
[45] Date of Patent: May 3, 1988

[54] BICYCLIC ALLYLETHER DERIVATIVES, PROCESSES FOR THEIR PRODUCTION AND THEIR USE

[75] Inventor: Anton Stütz, Maria Enzersdorf, Austria

[73] Assignee: Sandoz Ltd., Basel, Switzerland

[21] Appl. No.: 905,087

[22] Filed: Sep. 8, 1986

[30] Foreign Application Priority Data

Sep. 14, 1985 [DE] Fed. Rep. of Germany ....... 3532861

[51] Int. Cl.$^4$ .................. C07F 7/02; C07D 209/02; C07D 333/52; C07C 41/00; A61K 31/38; A61K 31/34
[52] U.S. Cl. .................. 514/414; 514/418; 514/432; 514/438; 514/443; 514/445; 514/456; 514/460; 514/469; 514/470; 514/717; 514/720; 548/406; 548/467; 548/484; 548/486; 548/509; 549/4; 549/23; 549/51; 549/52; 549/56; 549/58; 549/60; 549/214; 549/399; 549/401; 549/407; 549/462; 549/466; 549/471; 568/626; 568/659; 568/661; 568/663
[58] Field of Search .................. 549/78, 58, 4, 23, 51, 549/52, 56, 60, 214, 399, 401, 407, 462, 466, 471; 514/443, 438; 548/406, 467, 509, 484, 486; 568/659

[56] References Cited

FOREIGN PATENT DOCUMENTS

| 0024587 | 3/1981 | European Pat. Off. ............ 514/443 |
| 3442529 | 5/1986 | Fed. Rep. of Germany ...... 514/443 |
| 2116171 | 9/1983 | United Kingdom ................ 514/443 |

Primary Examiner—Alan Siegel
Attorney, Agent, or Firm—Gerald D. Sharkin; Robert S. Honor; Thomas O. McGovern

[57] ABSTRACT

Compounds of formula I

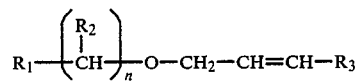

I wherein $R_1$ represents a group of formula

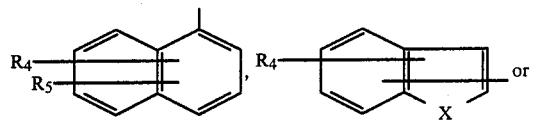

IIa   IIb

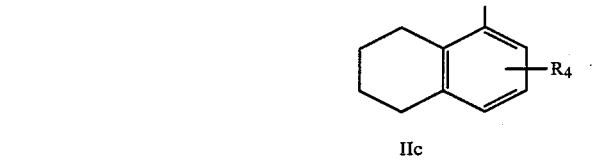

IIc whereby
$R_4$ and $R_5$ are the same or different and represent hydrogen, halogen, lower alkyl, lower alkoxy or trifluoromethyl and X represents oxygen, sulfur, imino, lower alkylimino, —(CH$_2$)—, —(S.CH$_2$)— or —(O.CH$_2$)—,
$R_2$ represents hydrogen or lower alkyl,
$R_3$ represents a group of formula

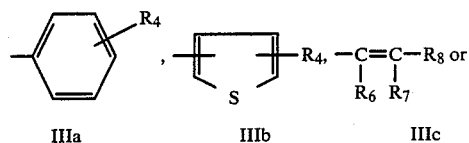

IIIa   IIIb   IIIc

—C≡C—R$_9$

IIId whereby
$R_6$, $R_7$ and $R_8$ are the same or different and represent hydrogen or alkyl or $R_6$ together with $R_7$ or $R_7$ together with $R_8$ represent —(CH$_2$)$_m$— wherein m is 3 to 6,
$R_9$ represents alkyl, alkenyl, trialkylsilyl or alkyl substituted by hydroxy, lower alkoxy, lower halogenalkyl or aryl and
n stands for 1, 2 or 3,
which possess pharmaceutical in particular antimycotic activity as well as activity against phytopathogenic fungi.

5 Claims, No Drawings

BICYCLIC ALLYLETHER DERIVATIVES, PROCESSES FOR THEIR PRODUCTION AND THEIR USE

The invention concerns bicyclic allyl ethers, processes for their production, pharmaceutical and agrochemical compositions containing them and their use as pharmaceuticals and agrochemicals especially antimycotics and fungicides.

More particularly the invention concerns compounds of formula I $$R_1-(CH)_n-O-CH_2-CH=CH-R_3 \quad \text{I}$$
$$\phantom{R_1-()}{}^{|R_2|}$$

wherein $R_1$ represents a group of formula

IIa, IIb or

IIc whereby
$R_4$ and $R_5$ are the same or different and represent hydrogen, halogen, lower alkyl, lower alkoxy or trifluoromethyl and X represents oxygen, sulfur, imino, lower alkylimino, —(CH$_2$)—, —(S.CH$_2$)— or —(O.CH$_2$)—,
$R_2$ represents hydrogen or lower alkyl,
$R_3$ represents a group of formula IIIa, IIIb, IIIc $$-C\equiv C-R_9 \quad \text{IIId}$$

whereby
$R_6$, $R_7$ and $R_8$ are the same or different and represent hydrogen or alkyl or $R_6$ together with $R_7$ or $R_7$ together with $R_8$ represent —(CH$_2$)$_m$—
wherein m is 3 to 6,
$R_9$ represents alkyl, alkenyl, trialkylsilyl or alkyl substituted by hydroxy, lower alkoxy, lower halogenalkyl or aryl and
n stands for 1, 2 or 3.

The compounds of formula I according to the invention may exist in free form or in the form of an acid addition salt e.g. with an organic or inorganic acid.

Lower alkyl moieties contain preferably 1 to 4 especially 2 or 1 carbon atoms.

Alkyl moieties preferably contain 1 to 12, particularly 2 to 6 especially 2 to 4 carbon atoms. Alkenyl substituents contain preferably 3 to 6 especially 3 or 4 carbon atoms e.g. allyl or propenyl. Alkyl and alkenyl moieties can be branched or straight chained. Aryl is preferably optionally substituted phenyl in particular a group of formula IIa. $R_4$ and $R_5$ are suitably the same and represent hydrogen or halogen. X is preferably sulfur, imino or lower alkylimino.

$R_1$ is preferably a group IIb or especially IIa.

$R_2$ is preferably hydrogen.

Halogen stands for fluorine, chlorine or bromine preferably chlorine or bromine.

$R_9$ is preferably alkyl especially lower alkyl in particular t-butyl.

According to the invention the compounds of formula I may be prepared by reacting a compound of formula $$R_1-(CH)_n-A \quad \text{IV}$$
$$\phantom{R_1-()}{}^{|R_2|}$$

with a compound of formula V $$A-CH_2-CH=CH-R_3 \quad \text{V}$$

wherein $R_1$, $R_2$, $R_3$ and n have the above meanings and one A represents hydroxy and the other a leaving group, and recovering the compounds thus obtained in free form or in acid addition salt form.

The process according to the invention can be carried out in a manner conventional for etherification reactions for example in an inert solvent e.g. an ether such as tetrahydrofuran (THF) or a dialkylamide such as dimethylformamide (DMF) at temperatures of for example 0° to boiling point of the reaction mixture preferably at room temperature. Salts may be prepared in conventional manner and free and salt forms interconverted.

Leaving group A is also conventional and is suitably iodine or preferably bromine or chlorine, or an organic sulfonyloxy radical with 1 to 10 carbon atoms for example alkylsulfonyloxy, preferably with 1 to 4 carbon atoms such as mesyloxy or alkylphenylsulfonyloxy preferably with 7 to 10 carbon atoms such as tosyl.

Insofar as the preparation of starting materials is not described they are either known or may be prepared analogously to known processes or processes herein described.

End products and starting materials may be isolated and purified in conventional manner.

The compounds of formula I and corresponding starting materials can be obtained in the form of mixtures of the various cis/trans isomers which can be separated in conventional manner or alternatively obtained by employing the corresponding isomer of the starting material. The invention is intended to cover all forms whereby isomeric mixtures are always referred to unless otherwise mentioned.

The compounds of the invention possess interesting chemotherapeutic in particular antimycotic activity and are therefore useful as pharmaceuticals in particular as antimycotics. The antimycotic activity can be established in vitro on various families and species of mycetes including Trichophyton spp, Aspergillus spp., Microsporum spp., Sporothrix spp. and Candida spp. e.g. in series dilution tests at concentrations of 0.01 to 100 μg/ml and in vivo in the experimental skin mycosis model on guinea pigs. In this latter test guinea pigs are infected by percutaneous application of *Trichophyton quinckeanum*. The test substance is administered during 7 days starting 24 hours after infection; either by local application of the test substance-(taken up in polyethyleneglycol) to the skin surface or peroral or subcutaneous application of the test substance as a suspension. The activity on local application was established at concentrations of 0.01 to 0.5% and the oral activity at dosages of e.g. 10 to 70 mg/kg body weight.

For the above mentioned use, the dose administered will, of course, vary depending on the compound employed, mode of administration and treatment desired. However, in general, satisfactory results are obtained when administered at a daily dosage of from 1 to 30 mg/kg of animal body weight, conveniently given in divided doses two to four times daily, or in controlled release form. For larger mammals having an approximate body weight of 70 kg the corresponding daily dosage is for example in the range of from 70 to 2000 mg; dosage forms suitable for e.g. oral administration comprise from 17.5 to 1000 mg of active ingredient.

The compounds of the invention may be administered in similar manner to known standards for use in such indications.

A suitable daily dosage will depend on a number of factors such as relative potency of activity. It has for example been determined in the experimental skin mycosis model that the preferred compound according to the invention (E)-(6,6-dimethyl-2-hepten-4-in-1-yl)-(1-naphthylmethyl)ether exhibited a curative dosage (i.e. dosage at which all guinea pigs infected with *Trichophyton mentagrophytes* var. *quinckeanum* 158 are mycologically cured) of 9×20 mg/kg in Miglyol compared with 9×70 mg/kg for Griseofulvin.

It is therefore indicated that the compounds be administered at similar or lower dosages than conventionally employed for Griseofulvin.

The compounds of the invention may be employed in the free base form or in the form of pharmaceutically acceptable acid addition salts. In general the salt forms exhibit the same order of activity as the free base forms. Examples of such acid addition salts include the hydrochloride, hydrogenfumarate and naphthaline-1,5-disulfonate.

The compounds may be admixed with conventional pharmaceutically acceptable diluents and carriers, and, optionally other excipients and administered orally, topically, i.v. or parenterally in such forms as tablets, capsules, creams, tinctures or injectable preparations.

Such compositions also form part of the invention.

The invention also concerns a method of combatting infections and diseases caused by mycetes comprising administering to a subject in need of such treatment an effective amount of a compound of formula I in free base form or in the form of a pharmaceutically acceptable salt thereof and such compounds for use as pharmaceuticals, in particular as anti-mycotic agents.

The compounds of the invention in free form or in agriculturally acceptable salt or metal complex form are also suitable for combatting phytopathogenic fungi. This fungicidal activity can be demonstrated i.a. in in vivo tests against *Uromyces appendiculatus* (bean rust) on runner beans as well as against other rust fungi (e.g. Hemileia, Puccinia) on coffee, wheat, flax and ornamentals (e.g. pelargonium, snapdragon); and against *Erysiphe cichoracearum* on cucumber as well as against other powdery mildews (e.g. E. Graminis f. sp. tritici. E. gram. f. sp. hordei, *Podosphaera leucotricha, Uncinula recator*) on wheat, barley, apple and vines.

The following examples illustrate the invention. All temperatures are given in degrees centigrade.

EXAMPLE 1

(E)-(6,6-Dimethyl-2-hepten-4-in-1-yl)-(1-naphthylmethyl)ether 5 g of 1-(Hydroxymethyl)naphthalin are in THF are treated at room temperature with 900 mg of 80% NaH (dissolved in mineral oil) and stirred until the evolution of gas ceases (ca. 1 hr.). A solution of 6.36 g of (E)-1-bromo-6,6-di-methyl-2-hepten-4-ine in DMF are added dropwise and the reaction mixture stirred overnight at room temperature.

The solvent is then largely evaporated off, the residue partitioned between ether and saturated aqueous Na-Cl, the organic phase dried and concentrated in vacuum. The residue is chromatographed over silica gel (eluent hexane/ethylacetate=98/2) and the title compound obtained as an oil.

The following compounds of formula I may be obtained analogously.

| Ex. | $R_1$ | n | $R_2$ | $R_3$ | Config. | |
|---|---|---|---|---|---|---|
| 2 | naphthyl | 1 | H | $-C\equiv C-C(CH_3)_3$ | Z | oil |
| 3 | " | 1 | H | $-C_6H_5$ | E | oil |
| 4 | chlorobenzothiophene | 1 | H | $-C\equiv C-C(CH_3)_3$ | E | oil |

-continued

| | | | | | |
|---|---|---|---|---|---|
| 5 | 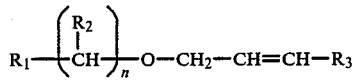 | 2 | H | " | E oil |
| 6 | " | 1 | H | 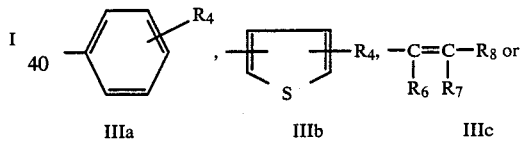 | E oil |
| 7 | " | 2 | H | —C₆H₅ | E oil |

NMR - Spectra

| Ex. | Spectrum: |
|---|---|
| 1 | 8.0–8.2(m,1H);7.76–7.95(m,2H);7.2–7.6(m,4H);6.16(dt, J = 16 and 2 × 5,5Hz,1H);5.75(dt,J = 16 and 2 × 1,5Hz,1H); 4.94(s,2H);4.1(dd,J = 5,5 and 1,5Hz,2H);1.23(s,9H). |
| 2 | 8.05–8.2(m,1H);7.65–7.95(m,2H);7.3–7.6(m,4H);6.05(dt, J = 11 and 2 × 6Hz,1H);5.67(dt,J = 11 and 1,5Hz,1H);4.98 (s,2H);4.36(dd,J = 6 and 1,5Hz,2H);1.22(s,9H). |
| 3 | 8.05–8.25(m,1H);7,2–8,0(m,11H);6.2–6.8(ABX₂-System, $J_{AB}$ = 16Hz);4.04(s,2H);3.3(d,J = 5Hz,2H). |
| 4 | 7.75–7.90(dd,J = 7 and 2,5Hz,1H);7.3–7.55(m,3H);6.15 (dt,J = 16 and 2 × 6Hz,1H);5.75(dt,J = 16 and 2 × 1,5Hz, 1H);4.80(s,2H);4.05(dd,J = 6 and 1,5Hz,2H);1.24(s,9H). |
| 5 | 8,0–8.2(m,1H);7.6–7.95(m,2H);7.25–7.6(m,4H);6.1(dt, J = 16 and 2 × 5.5Hz,1H);5.68(dt,J = 16 and 2 × 1Hz,1H); 4.02(dd,J = 5.5 and 1Hz);3.7–3.9(m,2H);3.3–3.5(m,2H); 1.22(s,9H). |
| 6 | 8.0–8.2(m,1H);7.7–7.95(m,2H);7.2–7.65(m,4H);6.16(dt,J = 16 and 2 × 6Hz,1H);5.76(dt,J = 16 and 2 × 1,5Hz,1H);4.97(s, 2H);4.1(dd,J = 6 and 1,5Hz,2H);1.44(qua,J = 7Hz,2H);1.18 (s,6H);0.98(t,J = 7Hz,3H). |
| 7 | 8.0–8.2(m,1H);7.7–7.9(m,2H);7.2–7.6(m,9H);6.1–7.7(AB- Part of an ABX₂-System,$J_{AB}$ = 16Hz,$J_{AX2}$ = 16Hz,$J_{AX2}$ = 5,5Hz,2H);4.18(J = 5,5Hz,2H);3.3–3.95(m,4H). |

We claim:

1. A compound of formula I

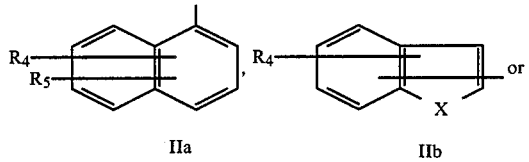

wherein R₁ represents a group of formula

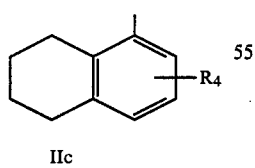

whereby

R₄ and R₅ are the same or different and represent hydrogen, halogen, lower alkyl, lower alkoxy or trifluoromethyl and X represents oxygen, sulfur, imino, lower alkylimino, —(CH₂)—, —(S.CH₂)— or —(O.CH₂)—, R₂ represents hydrogen or lower alkyl, R₃ represents a group of formula

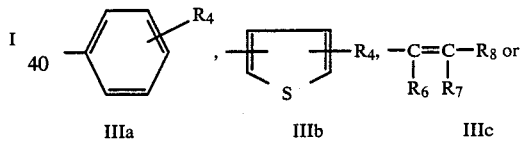

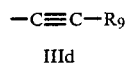

whereby

R₆, R₇ and R₈ are the same or different and represent hydrogen or alkyl or R₆ together with R₇ or R₇ together with R₈ represent —(CH₂)ₘ— wherein m is 3 to 6,

R₉ represents alkyl, alkenyl, trialkylsilyl or alkyl substituted by hydroxy, lower alkoxy, lower halogenalkyl or aryl and n stands for 1, 2 or 3, in free form or in the form of an acid addition salt.

2. A compound according to claim 1 selected from the group consisting of:

E-(6,6-dimethyl-2-hepten-4-in-1-yl)-(1-naphthylmethyl)ether;

Z-(6,6-dimethyl-2-hepten-4-in-1-yl)-(1-naphthylmethyl)ether;

E-(3-phenylallyl)-(1-naphthylmethyl)ether;

E-(6,6-dimethyl-2-hepten-4-in-1-yl)-(3-chloro-7-benzo[b]thienylmethyl)ether; or

E-(6,6-dimethyl-2-hepten-4-in-1-yl)-(1-naphthylethyl)ether.

3. A compound according to claim 1 selected from the group consisting of:
   E-(6,6-dimethyl-2-octen-4-in-1-yl)-(1-naphthylmethyl)ether; or
   E-(3-phenylallyl)-(1-naphthylethyl)ether.

4. A pharmaceutical composition comprising an antimycotic effective amount of a compound of formula I according to claim 1 in free form or in pharmaceutically acceptable acid addition salt form together with a pharmaceutically acceptable diluent or carrier.

5. A method of combatting infection and diseases caused by mycetes comprising administering to a subject in need of such treatment an antinycotic effective amount of a compound of formula I according to claim 1 in free form or in pharmaceutically acceptable acid addition salt form.

* * * * *